United States Patent [19]

Pitre

[11] Patent Number: 4,854,868
[45] Date of Patent: Aug. 8, 1989

[54] DENTAL ARTICULATOR

[76] Inventor: Evard M. Pitre, 6722 Hendon, Houston, Tex. 77074

[21] Appl. No.: 94,517

[22] Filed: Sep. 9, 1987

[51] Int. Cl.⁴ .............................................. A61C 11/00
[52] U.S. Cl. ......................................... 433/60; 433/59
[58] Field of Search .................................... 433/59, 60

[56] References Cited

U.S. PATENT DOCUMENTS

| | | | |
|---|---|---|---|
| 664,830 | 1/1901 | Bryan | 433/60 |
| 1,540,639 | 6/1925 | Lentz | 433/59 |
| 2,365,475 | 12/1944 | Klein | 433/60 |
| 2,731,723 | 1/1956 | Brandhandler | 433/60 |
| 3,808,689 | 5/1974 | Spinella | 433/60 |
| 4,263,715 | 4/1981 | Lampert | 433/60 |
| 4,337,039 | 6/1982 | Martin et al. | 433/60 |
| 4,462,801 | 7/1984 | Lagios | 433/60 |

FOREIGN PATENT DOCUMENTS 2718863 8/1978 Fed. Rep. of Germany ........ 433/60

Primary Examiner—Martin P. Schwadron
Assistant Examiner—Allen J. Flanigan
Attorney, Agent, or Firm—Browning, Bushman, Zamecki & Anderson

[57] ABSTRACT

A dental articulator has an anterior post having a C-shape to provide visual access to the front teeth. The upper and lower members of the articulator have dove-tail members for slidably receiving cup-like model carriers. The cup-like model carriers have sides of less than 360°, with a T-shaped beam on the bottom of the interior of the cup, and a pair of wedge-shaped beams on the bottom of the cup to slidably engage the dove-tail members. In alternative embodiments, the cup-like model carriers are bolted to the articulator, and can be rotatably indexed thereto.

14 Claims, 4 Drawing Sheets

DENTAL ARTICULATOR

BACKGROUND OF THE INVENTION

1. Field of the Invention

This invention relates, generally, to a dental articulator, and in particular, to an articulator having new and improved mechanisms for handling the plaster of paris or other molding material, and also relates to a new and improved anterior post which provides a clear visibility of the anterior teeth and the enhanced capability for working on the anterior teeth.

2. Description of the Background

The articulator disclosed herein is useful in all types of restoration work, but has been particularly designed for crown and bridge work. Tooth restoration work in dentistry is presently more or less divided between dentures that are removable from the mouth for cleaning and tooth restorations that are generally fixed to the teeth. These latter are known as crowns and fixed bridges.

When a dentist desires to prepare crowns or fixed bridges, he prepares the natural tooth by grinding to a suitable form to allow for sufficient bulk of metal or porcelain when the metal or porcelain is fabricated into crown and cemented into place over the prepared natural tooth. The dentist then takes an impression of that part of the mouth in which he has been working and then an impression of the teeth opposite that part of the mouth in which he has been working. The dentist then takes a wax bite of the entire area involved. The wax bite uses a material composed of two thin pieces of flat wax of approximately fourteen gauge in thickness with a sheet of tin foil or cellophane between the sheets. This bite is placed between the occluding surfaces of the teeth, and the patient then bites down into the wax to register the relationship between the upper and the lower jaw.

These impressions of the mouth are then used as molds and are filled with a material commonly referred to as dental stone because of its extreme hardness. When the stone has set up sufficiently hard, it is removed from the molds or impressions of the mouth, and the dentist then has a more or less perfect reproduction of the various teeth of the area in which he is working, including the grounddown tooth which is to be fitted with a crown or fixed bridge. The wax bite is then placed between the teeth formed of the dental stone to obtain the registry of the upper and lower jaws with each other. This combination of upper and lower jaws with the wax bite between them is then mounted on an articulator by covering the surfaces of both upper and lower jaw and by covering the surfaces of the lower member of the articulator and the upper member of the articulator with plastic of paris or similar material, which sets up all the upper and lower jaw impressions in perfect registry. The wax bite is then removed, and the casts of the teeth are now ready for building the desired kind of restoration in the conventional manner.

The gold or porcelain crown is then prepared in the usual fashion (usually by the lost wax method), and when completed it is then mounted on the cast of the prepared tooth or teeth, and the dentist or technician then checks the gold or porcelain crown for a proper fit. The human jaw has various normal motions, one of which is a forward and backward movement of the jaws relative to each other. The newly prepared crown must then be checked for such movement. Also, one of the normal movements of the human jaw is lateral or sideways movement of the teeth with respect to each other, and the dentist or technician must then next check the gold or porcelain crown for a proper clearance and freedom from obstruction by this lateral movement.

Typical of the prior art in this area is that of U.S. Pat. Nos. 1,319,737 to Wadsworth; 1,471,019 to Wilson: 2,697,279 to Clawson; and 4,175,325 to Beckwith.

It is known, for example, in U.S. Pat. No. 4,175,325 to Beckwith, to place the plaster of paris directly on the lower bow of the articulator. However, the plaster of paris will then harden on the articulator and become very difficult to clean up. Moreover, with no means for retaining the plaster of paris, it will tend to slump and fall off on the surrounding surfaces and in general be very messy.

Those in the art have also used an adjustable anterior post which will provide for the optimum vertical distance between the upper and lower sets of teeth. However, the prior art anterior posts have provided an obstruction to working on the anterior teeth.

It is therefore the primary object of the present invention to provide a new and improved articulator which allows the models to be more easily removed from the articulator.

It is another object of the present invention to provide a new and improved means in a dental articulator for maintaining the optimum vertical distance between the upper and lower teeth being manipulated.

It is yet another object of the present invention to provide a new and improved anterior post for use with a dental articulator for improving the visual access to the front teeth.

It is still another object of the present invention to provide a new and improved model holder for use with a dental articulator.

SUMMARY OF THE INVENTION

The objects of the invention are accomplished, generally, by the provision of a dental articulator which uses cup-shaped model holders having sides of less than 360°. As additional features, the model holders can be slidably attached or can be bolted to the articulator. Means are also provided for holding the models within the model holders and for rotatably indexing the model holder to the articulator.

Still other objects are accomplished by the provision of an anterior post having at least one vertical section and at least one section transverse or offset from the vertical.

BRIEF DESCRIPTION OF THE DRAWINGS

The objects, features and advantages of the present invention will become apparent when reading the following detailed description in conjunction with the accompanying drawings, in which.

DETAILED DESCRIPTION OF THE PREFERRED EMBODIMENT

Figure 1:
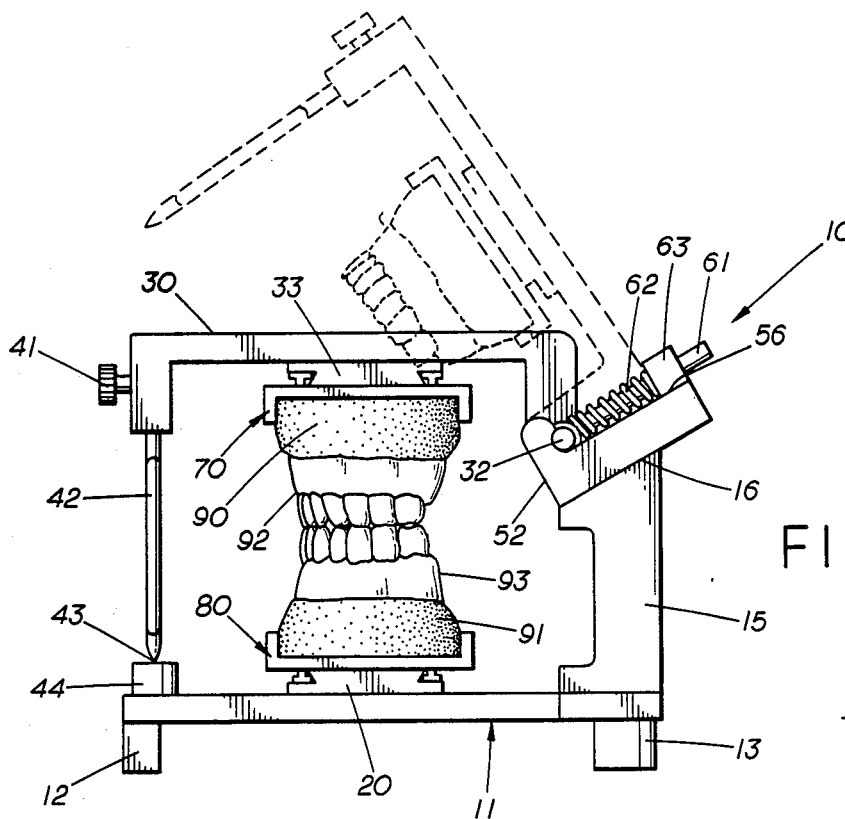
FIG. 1 is a side elevation, pictorial view of the articulator in accordance with the present invention, with the upper member illustrated in two positions.
Figure 2:
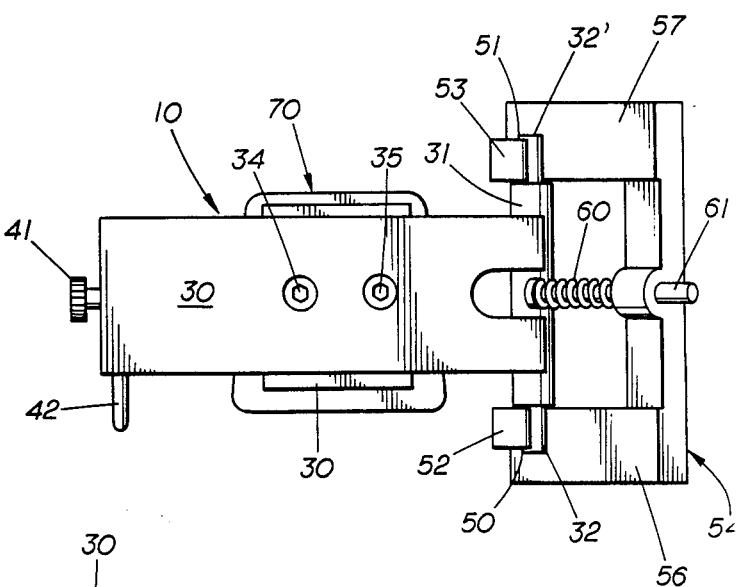
FIG. 2 is a top pictorial view of the articulator in accordance with the present invention.

Referring now to FIGS. 1-7, the articulator 10 has a lower T-shaped base member 11 having three support legs, two (12 and 13) of which are illustrated. Integral with the base member 11 is a pair of upright stems 14 and 15, together constituting a vertical stem section. The third support leg (not illustrated) is beneath the stem 14 in the same manner as leg 13 lies beneath the stem 15. As can best be seen in FIG. 1, the stems 14 and 15 are generally shaped like the numeral 1, each having a sloped upper surface with an angle of approximately 30° off horizontal. The stem 15 has the sloped upper surface 16.

A dove-tailed member 20 is attached to the base member 11 by means of screws (not illustrated) or by any other convenient means, for example, by welding, soldering, or even by gluing if one chooses to make the articulator out of plastic instead of metal, or members 11 and 20 can be fabricated, if desired, as one unit.

A U-shaped upper member 30 is attached at one of its ends to a rotatable bar 31 having a round pin 32 at one end of bar 31 and a similar pin 32' at its other end. A dove-tail member 33 is attached to the lower side of the member 30 by screws 34 and 35. Alternatively, the members 30 and 33 can be secured together in the same fashion as members 11 and 20 discussed hereinabove.

One end of the member 30 has a hole (unnumbered) into which one end 40 of the C-shaped anterior post 42 is slidably fitted. The set screw 41 sets the distance the end 40 is moved into the hole, thus establishing the vertical distance between the upper and lower sets of teeth. The other end 43 of the post 42 has a knife-edge resting on the cylindrical post 44. The fact of the anterior post 42 having a C-shaped design allows a window to the anterior (the front) teeth. It should be appreciated that the post 42 can be rotated one-half turn to provide additional ease of working on the anterior teeth. Moreover, instead of having the illustrated C-shape, the post 42 can be V-shaped or U-shaped, or any other design in which the post has at least one vertical portion and at least one portion offset or transverse to the vertical, to provide a window to the anterior teeth.

The pins 32, 32' are located in the slots 50 and 51, respectively, of a pair of projections 52 and 53 on the rectangular housing 54. The housing 54 has a first pair of parallel arms 56 and 57 which are bolted to the sloped surfaces 16 and the similar surface on stem 14, respectively. The slope of the slots 50 and 51 corresponds to the slope of surface 16. The bar 31 is slidably connected through spring 60 by a rod 61 to the hole 62 in the projection 63. The spring 60 normally causes the pins 32 and 32' to remain all the way in the back of slots 50 and 51. By gripping the top of member 30, working against the spring 60, the dentist or dental technician can simulate the action of the jaw bones by moving the pins 32 and 32' along the slope of slots 50 and 51. Likewise, there is some lateral movement of the top member 30 because of the loose fit of rod 61 in the hole within projection 63.

Figure 4:
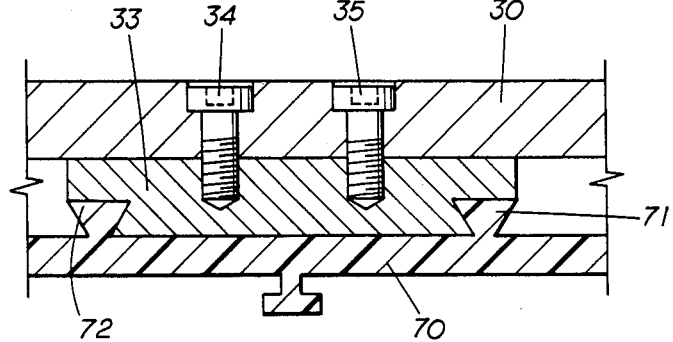
FIG. 4 is a side elevational view, in cross section, of the upper model holder slidably dove-tailed in place on the upper member of the apparatus according to the present invention.
Figure 3:
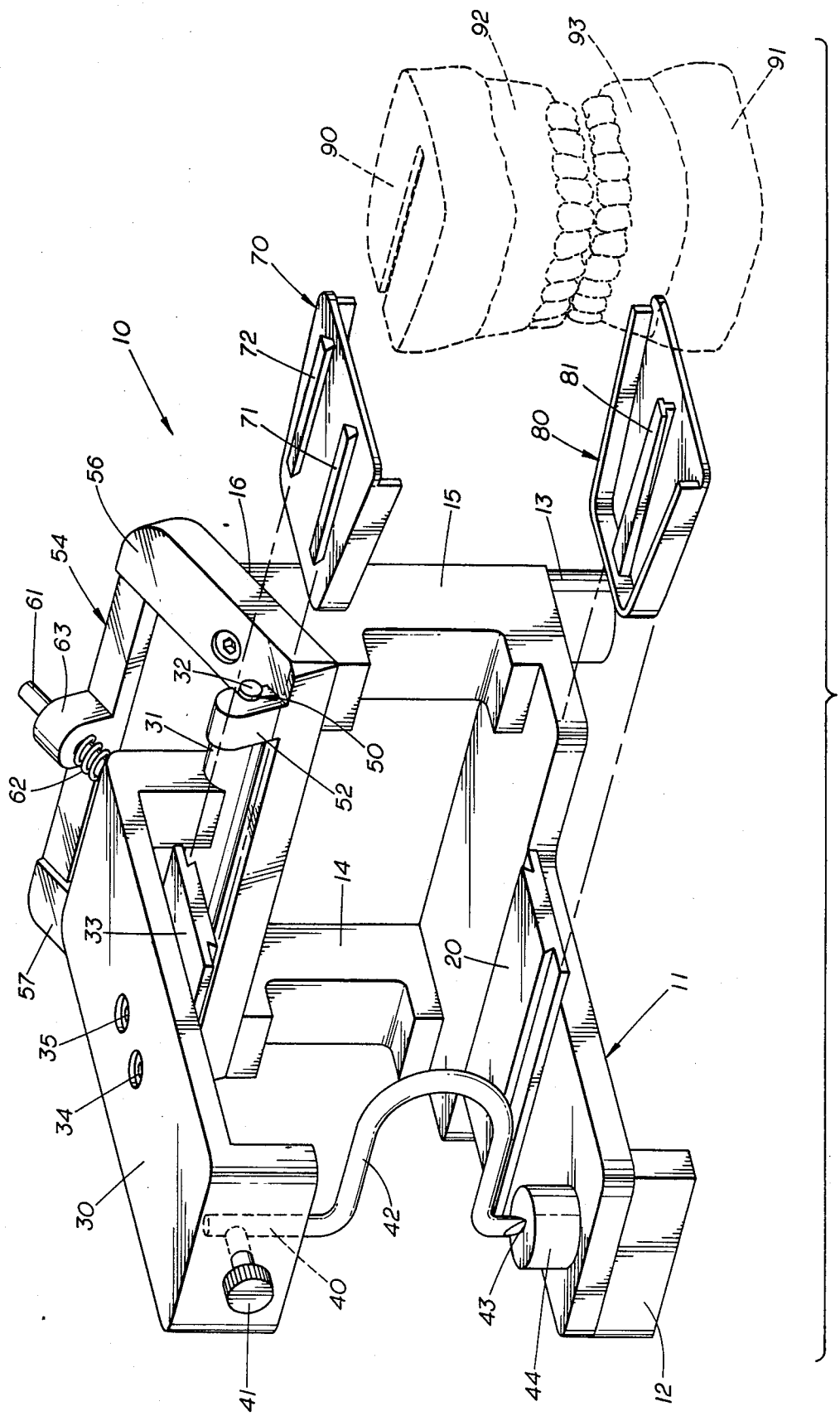
FIG. 3 is a pictorial view of the articulator according to the present invention, with the slidably removable model holders in an exploded position.

As illustrated in FIG. 3, and in cross section in FIG. 4, a model holder 70 having two wedge-shaped beams 71 and 72 is sized to slidably engage the dove-tail member 33. A similar model holder 80 has a pair of wedge-shaped beams 82 and 83 (illustrated in FIG. 6) sized to slidably engage the lower dove-tail member 20. The model carrier 80 is cup-shaped, with one side of the cup open, and has a single T-shaped beam on the bottom of the cup opposite its two wedge-shaped beams. By having a three-sided cup of less than 360°, the plaster of paris can slide out of the cup. Quite obviously, a round cup having a side portion of less than 360° will function in a similar, but not preferred manner. The purpose of the beam 81 is to lock the plaster of paris added to the cup. Unlike the prior art, the sides of the cups 70 and 80 will tend to keep the plaster of paris contained.

As is also illustrated in FIG. 3, showing the utility of the articulator 10, there is a first plaster of paris mold 90, a second plaster of paris mold 91, a cast 92 of the upper teeth and a cast 93 of the lower teeth.

Figure 5:
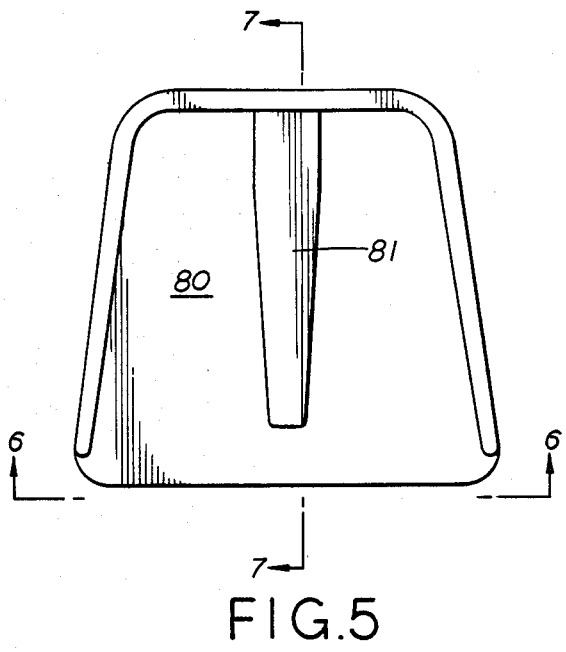
FIG. 5 is a top plan view of a model holder according to the present invention.
Figure 6:
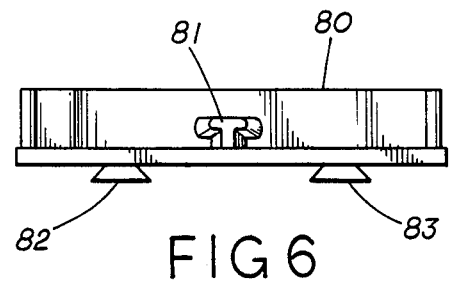
FIG. 6 is a side elevation, pictorial view of the model holder illustrated in FIG. 5.
Figure 7:
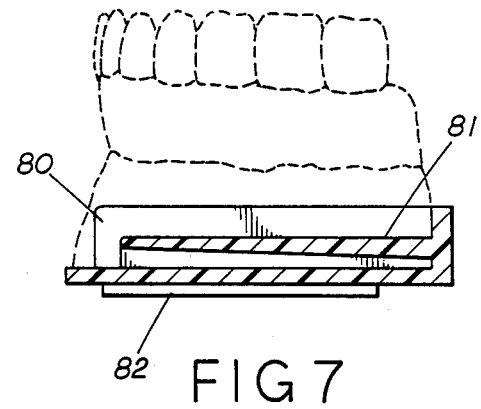
FIG. 7 is a side elevational view, partly in cross section, taken along the lines 7—7 of the model holder illustrated in FIG. 5.
Figure 11:
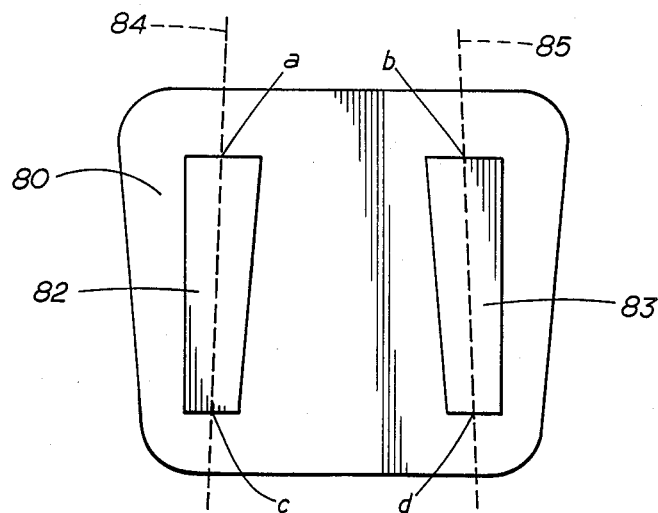
FIG. 11 is a bottom plan view of a model holder according to the present invention.

FIG. 11 illustrates a bottom plan view of the model holder illustrated in FIGS. 5-7. The model holder 80 has the two wedge-shaped beams 82 and 83. The respective longitudinal axis 84 and 85 of the two beams 82 and 83 are preferably molded so as to be converging at the open end of the holder 80, i.e., the distance between points a and b is shorter than the distance between points c and d.

In the operation of the model holder 80, in conjunction with the articulator illustrated in FIG. 3, the beams 82 and 83, by being further apart at points c and d, easily engage the dove-tailed member 20. As the beams 82 and 83 slide further along the member 20, the beams 82 and 83 are closer together and will firmly grasp the member 20, assuming the dove-tailed member itself has parallel sides. If desired, the beams 82 and 83 could be made to be parallel and the dove-tailed member 20 be made to have non-parallel sides. The same considerations apply to the model holder 70 and the dove-tailed member 33.

Figure 8:
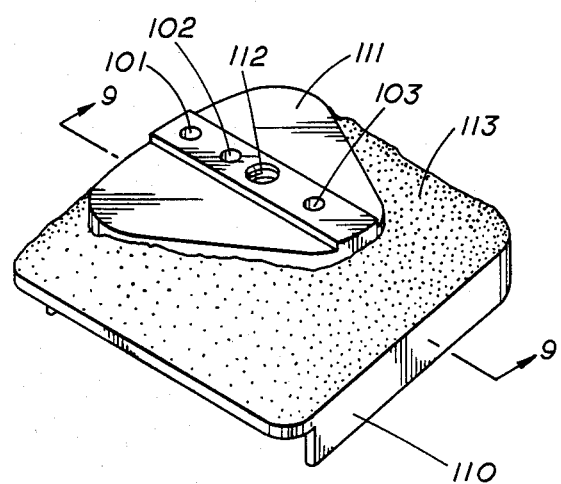
FIG. 8 is a pictorial, inverted view of a model holder according to an alternative embodiment of the present invention, including means to permanently mount the model holder to one of the members of the articulator.
Figure 9:
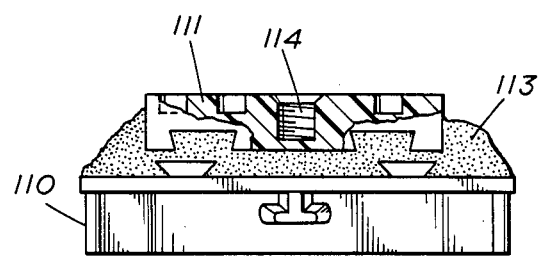
FIG. 9 is a side elevational view, partly in cross section, taken along the lines 9—9 of the model holder illustrated in FIG. 8.
Figure 10:
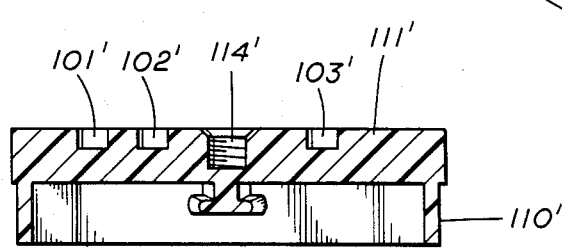
FIG. 10 is a side elevational view, partly in cross section, of yet another embodiment of a model holder in accordance with the present invention.

FIGS. 8, 9 and 10 illustrate an alternative embodiment of the invention, one in which the model carrier is not slidably engaged with the dove-tail member, but rather is attached to the lower member 11 by a bolt. The cup 110 has a plastic member 111 with a threaded hole 112 secured to the cup 110 by plaster of paris 113. A bolt 114 can then secure the cup 110 and member 111 to either the upper member 30 or lower member 11.

Alternatively, the cup 110 and plastic member 111 can be made in the plastic molding operation as one integral unit, without the use of the plaster of paris portion 113, as illustrated in FIG. 10. Thus, the sides 110' and bottom 111' of the model holder of FIG. 10 are one integral plastic unit. The bolt 114' allows the model holder to be bolted directly to either the upper member 30 or lower member 11.

Referring further to FIGS. 8–10 and 12, the members 111 and 111' are illustrated as having a plurality of holes 101, 102 and 103, and 101', 102' and 103', respectively.

Figure 12:
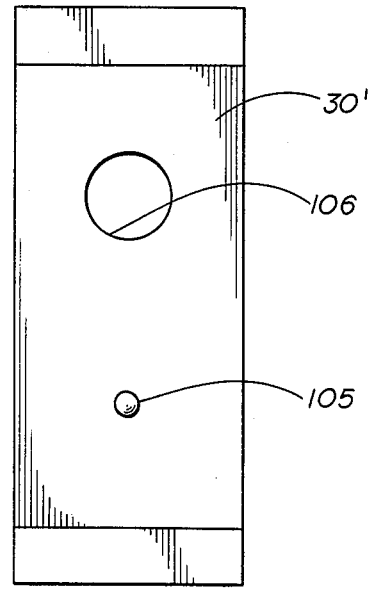
FIG. 12 is a bottom plan view of an alternative embodiment of the upper member of the articulator according the present invention.

By using a pin 105 on the member 30' of FIG. 12, the model holder illustrated in FIGS. 8 or 10 can be bolted to the threaded hole 106 by means of bolt 114 or 114' in one or two positions 180° apart. Thus, the pin 105 mates either with hole 101 or 103, or with hole 101' or 103'. By using other pin placements (not illustrated), the holder can be rotated to other positions. For example, by the use of a pin (not illustrated) on the radius of hole 102, measured from the bolt 106, the holder can be pinned at whatever the angle of the pin. By way of further example, by using a plurality of holes on the same radius, in conjunction with a single pin on that same radius, the holder can be rotatably indexed to any angle desired. Thus, the holder can be secured to either the upper or lower members at various angles. Those skilled in the art will recognize that the pin placements and holes can take on numerous patterns and angles.

In the operation of the articulator illustrated and described herein, it should be appreciated that by using the various cup-shaped model holders described herein, the dentist or dental technician is able to contain the plaster of paris, and is able to vastly improve the ease of removing the models from the articulator. Moreover, by providing the C-shaped anterior post, the dentist or dental technician can work on the anterior teeth in a much easier fashion.

What is claimed is:

1. A dental articulator, comprising:
    a vertical stem section;
    a lower base member connected to said vertical stem section, and a first dove-tail member mounted on said lower base member;
    an upper member pivotally connected to said vertical stem section, and a second dove-tail member mounted on said upper member;
    a first cup-like model carrier having an interior side and an exterior side and having a pair of wedge-shaped beams on its said exterior side sized to slidably engage said upper dove-tail member; and
    a second cup-like model carrier having an interior side and an exterior side and having a pair of wedge-shaped beams on its said exterior side sized to slidably engage said lower dove-tail member, each of said cup-like model carriers having single, continuous side portion only partially surrounding the perimeter of its said interior side and each of said cup-like model carriers also having at least one beam on its said interior side.

2. The dental articulator according to claim 1, including in addition thereto an anterior post between said lower base member and said upper member for controlling the vertical distance between said lower base member and said upper member.

3. The dental articulator according to claim 2, wherein said anterior post has at least one vertical section and at least one section transverse to the vertical.

4. The dental articulator according to claim 3, wherein said at least one transverse section of the anterior post is C-shaped.

5. A model holder for use with a dental articulator, comprising:
    a cup member having a bottom portion having an interior side and an exterior side and a single, continuous side portion only partially surrounding the perimeter of its said interior side; and
    at least one beam on the interior side of the said bottom portion.

6. The model holder according to claim 5, wherein said at least one beam comprises a single T-shaped beam.

7. The model holder according to claim 6, including in addition thereto, second and third beams on the exterior side of the said bottom portion.

8. The model holder according to claim 7 wherein said second and third beams are wedge-shaped and are non-parallel with respect to each other.

9. The model holder according to claim 5, wherein said exterior side of the bottom portion includes threaded bolt receiving means.

10. The model holder according to claim 9, including pin-receiving means for rotatably indexing the holder with respect to the dental articulator.

11. A dental articulator, comprising:
    a vertical stem section;
    a lower base member connected to said vertical stem section;
    an upper member pivotally connected to said vertical stem section;
    a first cup-like model carrier releasably attached to said upper members; and
    a second cup-like model carrier releasably attached to said lower member, each of said cup-like model carriers having an interior side and a single, continuous side portion only partially surrounding the perimeter of its said interior side and each of said model carriers also having at least one beam on its said interior side.

12. The dental articulator according to claim 11, including in addition thereto an anterior post between said lower base member and said upper member for controlling the vertical distance between said lower base member and said upper member.

13. The dental articulator according to claim 12, wherein said anterior post has at least one vertical section and at least one section transverse to the vertical.

14. The dental articulator according to claim 13, wherein said at least one transverse section of the anterior post is C-shaped.

* * * * *